United States Patent [19]

Orth et al.

[11] Patent Number: 4,567,272

[45] Date of Patent: Jan. 28, 1986

[54] PYRROLE CONTAINING 2-AMINONITROPYRIDINE DERIVATIVES

[75] Inventors: Winfried Orth, Hassloch/Pfalz; Werner Fickert, Mannheim, both of Fed. Rep. of Germany

[73] Assignee: Rütgerswerke Aktiengesellschaft, Frankfurt, Fed. Rep. of Germany

[21] Appl. No.: 649,336

[22] Filed: Sep. 11, 1984

[30] Foreign Application Priority Data

Sep. 21, 1983 [DE]  Fed. Rep. of Germany ....... 3334029

[51] Int. Cl.$^4$ ................. C07D 401/12; C07D 213/74; C07D 213/61
[52] U.S. Cl. .................................... 546/281; 546/297; 546/306; 546/307
[58] Field of Search ................ 546/281, 297, 306, 307

[56] References Cited

U.S. PATENT DOCUMENTS

| | | | |
|---|---|---|---|
| 2,657,212 | 10/1953 | Copp | 546/307 |
| 3,132,019 | 5/1964 | Soper | 546/307 |
| 3,634,439 | 1/1972 | Ayad | 546/307 |
| 3,862,157 | 1/1975 | Wiskott | 546/281 |

FOREIGN PATENT DOCUMENTS

| | | | |
|---|---|---|---|
| 1566125 | 5/1969 | France | 546/307 |
| 744281 | 2/1956 | United Kingdom | 546/307 |
| 750925 | 6/1956 | United Kingdom | 546/307 |

Primary Examiner—Henry R. Jiles
Assistant Examiner—Dale A. Bjorkman
Attorney, Agent, or Firm—Beveridge, DeGrandi & Weilacher

[57]  ABSTRACT

New 2-aminonitropyridine derivatives are disclosed of the formula:

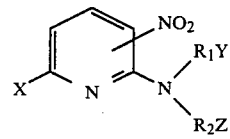

wherein
the nitro group is in the 3- or 5-position and X represents hydrogen, an alkoxy group with 1 to 3 C atoms or an unsubstituted or alkyl- or hydroxyalkyl substituted amino group, the alkyl portion of which has 1 to 3 C atoms $R_1$ and $R_2$ may be the same or different and represent hydrogen, divalent alkyl- with 1 to 3 C atoms, divalent cyclopropyl- or divalent alkenyl with 1 to 3 C atoms, phenylene- or divalent pyrrol and Y and Z may be the same or different and represent hydrogen, hydroxyl- or amino group of the formula II:

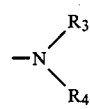

wherein $R_3$ and $R_4$ may be the same or different and represent hydrogen, an unsubstituted alkyl or alkyl with 1 to 3 C atoms, substituted at any position by hydroxy or amino with 1 to 3 C atoms, with the proviso that whenever X represents hydrogen, then $R_1$ and $R_2$ cannot both be hydrogen, and $R_1$ is not hydrogen, $R_2$ is not divalent alkyl-, pheneylene-, divalent cycloalkyl- or divalent heterocyclic group and $R_3$ and $R_4$ do not both signify hydrogen. The compounds are produced by conversion of halogen-, alkoxy- or sulfonic acid substituted nitropyridines with the corresponding amines. These compounds are pharmaceutical intermediates and nontoxic coupler components in oxidation hair dyes.

4 Claims, No Drawings

PYRROLE CONTAINING 2-AMINONITROPYRIDINE DERIVATIVES

The invention relates to new nitropyridine derivatives which in the 2-position have a primary, secondary or tertiary amino group. On the one hand, these compounds represent important pharmaceutical intermediate products, and unexpectedly, on the other hand they may be used as nontoxic coupler components in oxidation hair dyes and when so used they result in brilliant shades of color.

The nitropyridine derivatives of the invention are represented by the structural formula I:

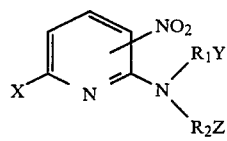  (I)

wherein
the nitro group is in the 3- or 5-position and X represents hydrogen, alkoxy of 1 to 3 C atoms or unsubstituted amino or alkyl- or hydroxyalkyl substituted amino, the alkyl portion thereof having from 1 to 3 C atoms, and $R_1$ and $R_2$ may be the same or different and represent hydrogen, divalent alkyl-, divalent cyclopropyl- or divalent alkenyl of 1 to 3 C atoms, divalent phenyl- or divalent pyrrol which is in turn substituted by Y and Z, and Y and Z may be the same or different and represent hydrogen, hydroxyl- or amino of the formula II:

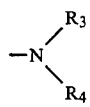  (II)

wherein
$R_3$ and $R_4$ may be the same or different and represent hydrogen, unsubstituted alkyl, alkyl or substituted at any position with a hydroxyl- or amino, the alkyl containing 1 to 3 C atoms, with the proviso that whenever X represents hydrogen; then $R_1$ and $R_2$ do not both signify hydrogen, $R_1$ does not signify hydrogen, and $R_2$ does not signify the residue of phenyl-, cyclopropyl- or pyrrolo; and $R_3$ and $R_4$ do not both signify hydrogen.

By the expression "divalent alkyl, divalent cyclopropyl or divalent alkenyl of 1 to 3 C atoms, divalent phenyl or divalent pyrrolo which in turn is substituted by Y and Z" is meant the divalent organic group which is obtained as a result of the stated monovalent organic group having lost an additional hydrogen and which, as a result, has an additional valence available for bonding to another substituent, viz. to Y and Z, respectively.

For example, when $R_1$ or $R_2$ is the divalent group —$CH_2$—(methylene), it may be considered to be a residue of the methyl group —$CH_3$; that is, a methyl group which has lost an additional hydrogen to become a divalent organic group and which is capable of substitution by Y and Z.

The nitropyridine derivatives of the invention are largely stable at ambient temperature against oxidation by the oxygen present in the air. They are soluble in water or in a mixture composed of water and a solvating agent such as, for example, ethyl alcohol.

In the compounds according to the invention, the nitro group may be present in either the 3- or 5-position.

X may represent hydrogen, a methoxy-, ethoxy-, propoxy-, i-propoxy group or an unsubstituted or alkyl- or hydroxyalkyl substituted amino group.

The amino group in the 2-position may be primary, secondary or tertiary amino. Whenever this amino group is secondary or tertiary, then the substituents $R_1$ and $R_2$ may be the same or different and may signify hydrogen, the residues of alkyl such as, for example, methylene-, ethylene-, propylene-, i-propylene, or phenylene- or heterocyclic group such as, for example, a pyrrolo group bonded to a C atom and, in turn substituted by Y and Z. These substituents on their part are substituted by the Y and Z substituents. Y and Z may be the same or different and may be either hydrogen, hydroxyl- or amino. Examples of such substituents are the following groups: hydroxymethyl-, hydroxyethyl- or hydroxypropyl-. The amino group is represented by the structural formula:

  (II)

in which $R_3$ and $R_4$ are the same or different and represent hydrogen, an unsubstituted alkyl with 1 to 3 C atoms or alkyl which is hydroxyl- or amine substituted at any given position.

Examples of this amino group are the unsubstituted amino group itself as well as methyl-, dimethyl-, ethyl-, diethyl-, methylethyl-, propyl-, i-propyl-, dipropyl-, diisopropyl-, aminomethyl-, aminoethyl-, aminopropyl-, bis-aminomethyl-, bis-aminoethyl-, bis-amino-propyl-, hydroxymethyl-, dihydroxymethyl-, hydroxyethyl-, dihydroxyethyl-, hydroxypropyl-, dihydroxypropylamino-, or pyrrol- or methylpyrrol.

However, whenever X is hydrogen, then the further limitation applies that $R_1$ and $R_2$ are not both hydrogen, $R_3$ and $R_4$ are not both hydrogen, and further that $R_1$ is not hydrogen and $R_2$ is not alkyl-, alkoxy-, phenyl-, cyclopropyl- or heterocyclic.

The nitropyridine derivatives of the invention are produced by conversion of the corresponding nitropyridine which in the 2-position has a group substitutable by amines with the designated amines. Such substitutable groups are alkoxy or sulfonic acid groups or halogens. The conversion reaction is carried out at 20°–100° C.

These starting nitropyridines are obtained in a preferred manner by nitration of the corresponding alkoxy or halogen alkoxy pyridines as described, for example, in the German patent application P No. 33 08 449.1 and the European application EP No. 0 102 652 A1. The conversion of these nitropyridines with the amines takes place in the course of a reaction requiring several hours of contacting the reactants with each other at ambient pressure and temperatures in the range of 20° to 100° C. At the same time, the reactants are intensively mixed with one another in a polar solvent such as, for example, water or in an alcohol. They are either dissolved in this reaction medium or are entirely or partially suspended or emulsified.

In general, the nitropyridine starting materials are prepared by nitration of halo-, alkoxy-, or haloalkoxypyridines. These reactions are described in "Pyridine And Its Derivatives" Part Two, pages 470-478 by E. Klingsberg, 1961, Interscience Publishers, Inc., N.Y.C., the disclosure of which is relied on and incorporated herein by reference.

The reactants may be used in equimolar quantities. For achieving a better yield however, it is advisable to use the less expensive aminocomponent in excess.

The end products obtained are insoluble in cold water and thus they may be separated in a cooled, aqueous reaction medium or in a reaction medium mixed with water.

The following examples serve to illustrate the invention without limiting it in any way.

EXAMPLE 1

2-(Dimethylaminoethyleneamino)-5-nitropyridine

A mixture of 154 g (1 mole) of 2-methoxy-5-nitropyridine, 105.8 g (1.2 mole) or 110 g of 95% N,N-dimethylethylenediamine as well as 200 ml of water is heated to reflux in the course of hours with stirring. Subsequently, an additional 100 ml of water are added and after cooling the crystallized product is filtered off with suction, washed with water and then dried. The yellow colored substance has a melting point of 94°–5° C. and is obtained in a yield of 89% of theory.

EXAMPLE 2

2-(N-hydroxyethyl-N-methylamino)-5-nitropyridine

A mixture of 154 g (1 mole) of 2-methoxy-5-nitropyridine, 90 g (1.2 mole) of N-methylethanolamine and 200 ml of water is heated to reflux for 8 hours with stirring. After cooling, the solid substance is filtered off with suction, washed with water and is then dried in the vacuum. An intensively yellow dyed product is obtained with a melting point of 83°–4° C. and in a yield of 78% of theory.

EXAMPLE 3

2-(dimethylaminotrimethyleneamino)-5-nitropyridine

A mixture of 154 g (1 mole) of 2-methoxy-5-nitropyridine, 132.8 (1.3 mole) of N,N-dimethyltrimethylenediamine as well as 200 ml of water is heated to reflux for 6 hours with stirring. After cooling off, the crystallized product is filtered off with suction. It is washed 3 times with 100 ml of water and dried. An intensively yellow colored powder with a melting point of 73°–4° C. is obtained in a yield of 83% of theory.

EXAMPLE 4

2-(hydroxyethylaminoethyleneamino)-5-nitropyridine

A mixture of 154 g (1 mole) of 2-methoxy-5-nitropyridine, 125 g (1.2 mole) of N-hydroxyethylethylenediamine and 200 ml of water is heated to reflux for 6 hours with stirring. After that, an additional 100 ml of water are added and the crystallized product is filtered off with suction, washed with water and then dried. An intensively yellow colored compound is obtained with a melting point of 146°–7° C., in a yield of 76% of theory.

EXAMPLE 5

2-(1-methyl-1H-pyrrol-2-yl-ethaneamino)-5-nitropyridine

To a stirred mixture of 158.6 (1 mole) of 2-chloro-5-nitropyridine and 200 ml of methanol, a mixture of 136.6 g (1.1 mole) of 1-methyl-1H-pyrrol-2-yl-ethaneamine and 121.4 g (1.2 mole) of triethylamine is added drop by drop in the course of 1 hour. After 6 hours, 300 ml of water are added, the crystallized product is filtered off by suction, washed with water and dried. A yellow colored substance with a melting point of 141°–2° C. is obtained in a yield of 98% of theory.

EXAMPLE 6

2-(1,5-dimethyl-1H-pyrrol-2-yl-methaneamino)-5-nitropyridine

To a stirred mixture of 158.6 g (1 mole) of 2-chloro-5-nitropyridine and 200 ml of methanol, a mixture of 136.6 g (1.1 mole) 1,5-dimethyl-1H-pyrrol-2-yl-methaneamine and 121.4 g (1.2 mole) of triethylamine are added drop by drop in the course of 2 hours, at the same time, the temperature is kept at 45°–50° C. by cooling. After 8 hours, 300 ml of water are added, the precipitated product is filtered off by suction, the suction cake is washed with ample water and is dried at 50° C. A yellow colored compound with a melting point of 163°–5° C. is obtained in a yield of 96% of theory.

EXAMPLE 7

2-(2-hydroxyphenylamino)-6-methoxy-3-nitropyridine

A mixture of 188.6 (1 mole) of 2-chloro-6-methoxy-3-nitropyridine and 262 g (2.4 mole) of o-aminophenol is heated in 500 ml of methanol gradually up to reflux. After heating for a period of 2 hours, the mixture is filtered off hot by suction; the suction cake is washed with enough methanol until the filtrate runs off practically colorless and is dried. Bright red crystals with a melting point of 206°–7° C. are obtained in a yield of 94.6% of theory.

EXAMPLE 8

2-(dimethylaminopropylamino)-6-methoxy-3-nitropyridine hydrochloride

To a suspension of 188.6 g (1 mole) of 2-chloro-6-methoxy-3-nitropyridine in 300 ml of methanol, 265.2 g (2.6 mole) of N,N-dimethylaminopropylene amine are added drop by drop while stirring and cooling. The mixture is stirred once more for another 2 hours after the addition of amine and then is poured into 300 ml of water, whereby the substance is obtained as a yellow oil. The oil is separated and is mixed twice more with water until the wash water layer appears only weakly yellow in color. It is then absorbed in isopropanol and is precipitated as the HCl salt by the introduction of HCl-gas. The salt is filtered off by suction and is washed with isopropanol and dried. The product is obtained in the form of luminously yellow colored crystals with a melting point of 186° C. and in a yield of 76% of theory.

EXAMPLE 9

6-methoxy-3-nitro-2-n-propylaminopyridine

Into a stirred and cooled (water bath) mixture of 188.6 g (1 mole) of 2-chloro-6-methoxy-3-nitropyridine and 200 ml of isopropanol, 141.9 g (2.4 mole) of n-propylamine are added drop by drop in the course of about 3 hours at a maximum temperature of 25° C. Stirring is continued overnight and then 1000 ml of water are added; the precipitated product is filtered off by suction, washed with water and then dried. The product obtained thereby is intensively yellow colored with a melting point of 69°–70° C. in a yield of 98% of theory.

EXAMPLE 10

2-(2-hydroxyethylamino)-6-methoxy-3-nitropyridine

To a mixture of 188.6 g (1 mole) of 2-chloro-6-methoxy-3-nitropyridine with 350 ml of isopropanol, 83.5 g (1.4 mole) of aminoethanol are added drop by drop with cooling while stirring and maintaining a temperature of 25°–30° C. After the addition, the reaction mixture is continued to be stirred for another hour at a maximum of 30° and then 47.5 ml of 50% caustic soda solution are added drop by drop over the course of about 2 hours at a maximum temperature of 30° C. After 6 hours of stirring, 500 ml of water are stirred in and the product is filtered off with suction, is then washed sufficiently with water and is then dried. The compound is obtained in the form of a yellow powder with a melting point of 121°–2° C. and in a yield of 95.5% of theory.

EXAMPLE 11

2-(3-hydroxyphenylamino)-6-methoxy-3-nitropyridine

A mixture of 188.6 g (1 mole) of 2-chloro-6-methoxy-3-nitropyridine and 262 g (2.4 mole) of m-aminophenol is heated in 500 ml of methanol gradually up to the reflux. After 2 hours of heating time, the mixture is cooled down, 1000 ml of water are stirred in, the crystals formed are filtered off by suction and are thoroughly washed with water. The compound is obtained in the form of orange colored crystals with a melting point of 156°–8° C. and in a yield of 97.7% of theory.

EXAMPLE 12

2,6-bis-(2-hydroxyethylamino)-3-nitro-pyridine

To a mixture of 188.5 g (1 mole) of 2-chloro-6-methoxy-3-nitropyridine and 500 ml of isopropanol, 220 g (3.6 mole) of monoethanolamine are added drop by drop during approximately 60 minutes. After the exothermal reaction has subsided, 200 ml of water are added and the resulting mixture is then heated for 10 hours under reflux. Then the isopropanol is distilled off, the excess base is neutralized by the addition of dry ice. During the cooling off to 5° C., the compound is precipitated, it is filtered off by suction, washed again with ice water and dried. The yield of intensively yellow colored product with a melting point of 130°–1° C. amounts to 94% of theory.

EXAMPLE 13

6-ethoxy-2-methylamino-3-nitropyridine

In a stirred mixture consisting of 202.6 g (1 mole) of 2-chlor-6-ethoxy-3-nitropyridine and 500 ml of methanol, 202 g (2.6 mole) of a 40% monomethylamine solution is added drop by drop while stirring in the course of 90 minutes and at 25°–30° C. sump temperature. Subsequently, the mixture is again stirred for yet another 5 hours, is reacted with 650 ml of water, and then the product is filtered off by suction, is washed again with ample water and dried. Melting point 106°–7° C., Yield: 183.2 g (92.9% of theory).

The compounds of the present invention can be used as nontoxic coupler components for human hair dyeing. When used in this way, they are combined with conventional developer compounds, such as a primary aromatic amine (e.g. p-phenylene diamine, p-aminophenol) which are known for this purpose in the hair dyeing art. Usually, the coupler compounds are used in the amount of 1–2% by weight in a hair dyeing composition, although the exact amount may vary. Methods and techniques for hair dyeing that are known in the art may be used in connection with the 2-aminopyridine derivatives of this invention.

Further variations and modifications of the present invention will become apparent to those skilled in the art from a reading of the foregoing and are intended to be encompassed by the claims appended hereto.

The German priority application P. No. 33 34 029.3 is relied on and incorporated herein by reference.

We claim:

1. A nitropyridine derivative represented by the structural formula:

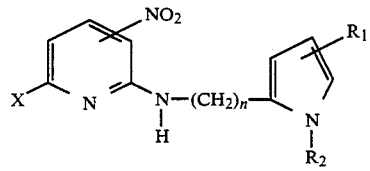

in which
the nitro group is in the 3- or 5-position and X represents hydrogen, an alkoxy group with 1 to 3 C atoms or an unsubstituted or alkyl- or hydroxyalkyl substituted amino group, the alkyl portion of which has 1 to 3 C atoms, $R_1$ and $R_2$ may be the same or different and represent hydrogen or a methyl-group and n is 0, 1, 2 or 3.

2. A nitropyridine derivative represented by the structural formula I:

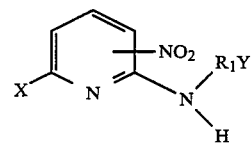

wherein
the nitro group is in the 3- or 5-position and X represents hydrogen, an alkoxy group with 1 to 3 C atoms or an unsubstituted or alkyl- or hydroxyalkyl substituted amino group, the alkyl portion of which has 1 to 3 C atoms, and $R_1$ is methylene, ethylene, propylene or isopropylene and Y is pyrrol or methypyrrol.

3. A nitropyridine derivative which is 2-(1-methyl-1H-pyrrol-2-yl-ethaneamino)-5-nitropyridine.

4. A nitropyridine derivative which 2-(1,5-dimethyl-1H-pyrrol-2-yl-methaneamino)-5-nitropyridine.

* * * * *